United States Patent [19]
Eller et al.

[11] Patent Number: 5,780,681
[45] Date of Patent: Jul. 14, 1998

[54] PREPARATION OF AMINES FROM OLEFINS OVER OXIDES OF GROUP IVB OR VIB OR MIXTURES THEREOF ON CARRIERS

[75] Inventors: Karsten Eller, Ludwigshafen; Rudolf Kummer, Frankenthal; Michael Hesse, Worms, all of Germany

[73] Assignee: BASF Aktiengesellschaft, Ludwigshafen, Germany

[21] Appl. No.: 869,759

[22] Filed: Jun. 5, 1997

[30] Foreign Application Priority Data

Jun. 18, 1996 [DE] Germany .................. 19624206.1

[51] Int. Cl.$^6$ .................................................. C07C 209/02
[52] U.S. Cl. .................................................. 564/485
[58] Field of Search .................................................. 564/485

[56] References Cited

U.S. PATENT DOCUMENTS 4,588,842  5/1986  Vanderpool .................. 564/479

*Primary Examiner*—Brian M. Burn
*Attorney, Agent, or Firm*—Keil & Weinkauf

[57] ABSTRACT

Amines of general formula I

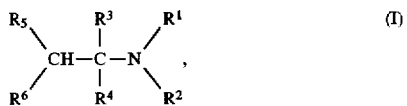

(I)

where $R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ together form a saturated or unsaturated $C_3$–$C_9$-alkylene chain and $R^3$ or $R^5$ is $C_{21}$–$C_{200}$-alkyl or $C_{21}$–$C_{200}$-alkenyl, or $R^3$ and $R^5$ together form a $C_2$–$C_{12}$-alkylene chain, are prepared by reacting an olefin of the general formula II

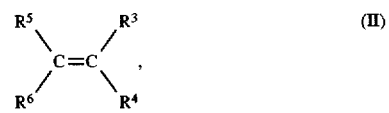

(II)

where $R^3$, $R^4$, $R^5$ and $R^6$ have the above-mentioned meanings, with ammonia or primary or secondary amines of the general formula III

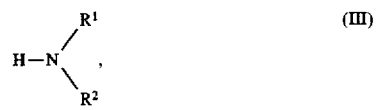

(III)

where $R^1$ and $R^2$ have the abovementioned meanings, at from 200° to 350° C. and from 100 to 300 bar in the presence of a heterogeneous catalyst, by a process in which the heterogeneous catalyst used is an oxide of group IVB or VIB or a mixture thereof on a carrier.

11 Claims, No Drawings

5,780,681

PREPARATION OF AMINES FROM OLEFINS OVER OXIDES OF GROUP IVB OR VIB OR MIXTURES THEREOF ON CARRIERS

DESCRIPTION

The present invention relates to a process for the preparation of amines by reacting ammonia or a primary or secondary amine with an olefin at elevated temperatures and superatmospheric pressure in the presence of oxides of group IVB or VIB or a mixture thereof on carriers.

An overview of the methods for the amination of olefins is given in "Functionalisation of Alkenes: Catalytic Amination of Monoolefins", J. J. Brunet et al. J. Mol. Catal. 49 (1989), 235–259.

There are in principle two catalytic mechanisms. The olefin is coordinated via a metal complex. This activated species can be attacked by the nucleophilic amine and can form a more highly aminated product. The amine may be chemisorbed at acid centers or metal centers (via metal amides) and can be reacted in this activated form with the olefin.

Suitable catalysts are zeolites. They have a large number of catalytically active centers in combination with a large surface area. The zeolites described differ in type and in the aftertreatment (for example thermal treatment, dealumination, acid treatment, metal ion exchange, etc.). Examples of these are to be found in U.S. Pat. No. 4,536,602, EP-A-101 921 or DE-A-42 06 992.

EP-A-133 938, EP-A-431 451 and EP-A-132 736 disclose processes in which borosilicate, gallosilicate, aluminosilicate and ferrosilicate zeolites are used for the preparation of amines from olefins, and the possibility of doping these zeolites with alkali metals, alkaline earth metals and transition metals is pointed out.

CA-A-2 092 964 discloses a process for the preparation of amines from olefins, in which BETA-zeolites, which are defined as crystalline aluminosilicates of a certain composition having a pore size of more than 5 Å, are used. Metal- or acid-modified beta-zeolites are preferably used.

A particular disadvantage of the zeolites as catalysts is their complex preparation and hence their high price. In the selective synthesis of a molecular sieve (for example of a zeolite) by hydrothermal synthesis, it is necessary exactly to maintain many parameters, for example the crystallization time, crystallization temperature, pressure or the aging steps. The structure-directing compound (template) usually used in a zeolite synthesis must be removed after the crystallization. As a rule, the template is removed by calcination, the organic compound being oxidatively degraded. For ecological and economic reasons, this must be considered to be very adverse.

The preparation of crystals of a certain size or morphology and the preparation of supported zeolites, which are often desirable as catalysts owing to the advantages in terms of process engineering, are generally possible only at great expense, if at all. The zeolites have a very narrow pore size distribution. The pore sizes vary from 4 to about 12 Å depending on the type of zeolite.

In a zeolite-catalysed reaction, only those molecules which are smaller than the pore dimensions have access to the catalytically active centers in the interior of the zeolite. Reactants having larger dimensions are excluded from the interior of the pores.

For the abovementioned amination reactions, this means that the catalytic centers in the interior of the zeolite are not available for the preparation of amines which are larger than the pore diameter.

It is an object of the present invention to remedy the abovementioned disadvantages, in particular to provide catalysts for the amination of olefins, the preparation of which is substantially simpler than that of the zeolite catalysts and which have an advantageous pore size distribution even for relatively bulky amine molecules.

The use of acid-modified montmorillonites is described in EP-A-469 719. The use of precipitated catalysts with combination of two or more metal oxides, excluding the combination of Si and Al, is described in JP-04082864.

DE-A-44 31 093 discloses oxidic catalysts which are prepared by means of the sol-gel process. The formation of gels is a metastable process and scale-up is therefore very difficult.

All processes for the synthesis of amines from olefins over non-zeolite catalysts have a low amine yield or low space-time yield or lead to rapid deactivation of the catalysts.

It is an object of the present invention to remedy these disadvantages.

We have found that this object is achieved by a novel and improved process for the preparation of amines of the general formula I

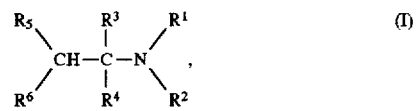

where
$R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ together form a saturated or unsaturated $C_3$–$C_9$-alkylene chain and $R^3$ or $R^5$ is $C_{21}$–$C_{200}$-alkyl or $C_{21}$–$C_{200}$-alkenyl, or $R^3$ and $R^5$ together form a $C_2$–$C_{12}$-alkylene chain, by reacting an olefin of the general formula II

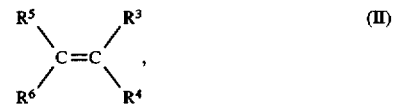

where $R^3$, $R^4$, $R^5$ and $R^6$ have the abovementioned meanings, with ammonia or a primary or secondary amine of the general formula III

where $R^1$ and $R^2$ have the abovementioned meanings, at from 200° to 350° C. and from 100 to 300 bar in the presence of a heterogeneous catalyst, wherein the heterogeneous catalyst used is an oxide of group IVB or VIB or a mixture thereof on a carrier.

The novel process may be carried out as follows:

The olefin II and ammonia or the primary or secondary amine III can be reacted at from 200° to 350° C., preferably from 220° to 330° C., particularly preferably from 230° to 320° C., and from 100 to 300, preferably from 120 to 300, particularly preferably from 140 to 290 bar in the presence of an oxide of group IVB or VIB or a mixture thereof on a carrier as a catalyst, for example in a pressure-resistant reactor, and, preferably, the amine obtained is separated off and the unconverted starting materials are recycled.

The present invention gives a very good yield in combination with high selectivity and high space-time yield. Moreover, the deactivation of the catalyst has been suppressed. The preparation of the catalyst is carried out in a simple and readily reproducible manner.

In the novel process, a high selectivity with respect to the desired reaction product is achieved with a small excess of ammonia or amine and the dimerization and/or oligomerization of the olefin used is avoided.

In an embodiment of this process, ammonia and/or amines III, mixed with the olefin II in a molar ratio of from 1:1 to 5:1, are fed to a fixed-bed reactor and reacted at from 100 to 300 bar and from 200° to 350° C. in the gas phase or in the supercritical state.

The desired product can be obtained from the discharged reaction mixture with the aid of known methods, for example distillation or extraction, and, if required, can be brought to the desired purity by means of further separation operations. The unconverted starting materials are, as rule, preferably recycled to the reactor.

Mono- or polyunsaturated olefins II, in particular those of 2 to 10 carbon atoms, or mixtures thereof and polyolefins may be used as starting materials. Owing to the small tendency to polymerization, monoolefins are more suitable than di- and polyolefins, but these may be converted just as selectively with the aid of a larger excess of ammonia or of an amine. The position of the equilibrium and hence the conversion to the desired amine are very greatly dependent on the reaction pressure chosen. High pressure favors the adduct, but in general the pressure range up to 300 bar is the optimum for technical and economic reasons. The selectivity of the reaction is influenced to a high degree by the temperature—in addition to parameters such as ammonia/amine excess and catalyst. Although the reaction rate of the addition reaction increases greatly with increasing temperature, competing crack and recombination reactions of the olefin are simultaneously promoted. Moreover, an increase in temperature is not advantageous from the thermodynamic point of view. The position of the optimum temperature with regard to conversion and selectivity is dependent on the constitution of the olefin, of the amine used and of the catalyst and is in general from 200° to 350° C.

Suitable catalysts for the amination of olefins are oxides of groups IVB and VIB of the Periodic Table of Elements or mixtures thereof ie. the oxides of titanium, zirconium, hafnium, chromium, molybdenum and tungsten, preferably oxides of zirconium and tungsten. Suitable carries are oxides such as $SiO_2$, $Al_2O_3$, $TiO_2$, $ZrO_2$, MgO, $Fe_2O_3$, $SnO_2$ or $CeO_2$ or mixtures such as $SiO_2$—$Al_2O_3$ or $SiO_2$—$TiO_2$, preferably $SiO_2$, $Al_2O_3$, $TiO_2$, $Fe_2O_3$, $SnO_2$, $CeO_2$ or mixtures such as $SiO_2$—$Al_2O_3$, carbides or nitrides, such as WC, SiC or $Si_3N_4$, sheet silicates, such as montmorillonite, kaolin, saponite or vermiculite, or mixtures thereof. Oxidic carriers, in particular those containing from 60 to 100% by weight of $SiO_2$, which have a BET surface area of, as a rule, from 100 to 1000, preferably from 120 to 600, $m^2g^{-1}$ after application of the oxides of group IVB and/or VIB, are preferred.

Among the oxides of groups IVB and VIB, $TiO_2$, $ZrO_2$, $HfO_2$, $Cr_2O_3$, $CrO_2$, $CrO_3$, $MoO_2$, $MoO_3$, $WO_2$ and $WO_3$ are preferred and $TiO_2$, $ZrO_2$, $MoO_3$ and $WO_3$ are particularly preferred, especially $ZrO_2$ and $WO_3$. The oxides may be used either as individual oxides or as a combination of two or more oxides, combinations of two oxides being preferred and a combination of an oxide of group IVB with an oxide of group VIB being particularly preferred. From this combination, the following are particularly noteworthy: $TiO_2$—$WO_3$, $TiO_2$—$MoO_3$, $ZrO_2$—$WO_3$ and $ZrO_2$—$MoO_3$, in particular $ZrO_2$—$WO_3$.

The oxidation states of the oxides may vary between the form as prepared and the form present under reaction conditions, readily reducible metal oxides, for example $MoO_3$, being partially or completely converted to lower oxidation states, eg. $MoO_2$, by the reaction mixture comprising ammonia, olefins and amines. A reduction preceding the reaction may also be used if, for example, the supported oxides are present in a high oxidation state after the calcination and a lower oxidation state is desired. For example, organic compounds, such as formaldehyde, oxalic acid, formic acid or isopropanol, or organic reducing agents, such as $NaBH_4$ or $NH_4HCO_2$ (ammonium formate), or hydrogen may be used as reducing agents. Hydrogen, either alone or diluted with an inert gas, such as nitrogen or argon, is preferred.

The amount of applied oxides of groups IVB and VIB depends on the choice of the oxides and of the carrier in each case. In general, an advantageous effect is obtained for the catalysis with amounts of only 1% by weight of metal of group IVB and/or VIB in the prepared catalyst, whereas more than 40% by weight generally produces only small improvements. Amounts of from 1 to 40% by weight of the metals of groups IVB or VIB or mixtures thereof per metal are therefore preferred, particularly preferably from 5 to 20% by weight of heterogeneous catalysts which contain from 5 to 15, preferably from 5 to 10, % by weight of tungsten and from 8 to 25, preferably 10 to 20, % by weight of zirconium on a carrier.

The metal oxides may be applied to the carriers by various methods. For economic reasons, steeping or impregnation is generally chosen, but other methods of preparation, for example chemical vapor deposition, are also possible. In a preferred variant, a solution of oxide precursors is added to the dried and hence anhydrous carrier so that the oxide precursor is uniformly distributed over the carrier. Also preferred is application by means of spray impregnation, in which the carrier is agitated and sprayed with a solution of the oxide precursor to be introduced by impregnation, so that a uniform distribution of the sprayed solution results.

The type of solution may differ; for example, alcoholic solutions may be used but, once again for economic reasons, aqueous solutions are generally chosen. Suitable oxide precursors are all compounds of groups IVB and VIB which can be subsequently converted into oxides. This conversion is preferably effected by calcination. For example, various, water-soluble salts, such as $TiOSO_4$, a hydrochloric acid-containing solution of $TiOCl_2$ or $TiCl_4$, $ZrO(NO_3)_2$, the water-soluble salts of tungstic acid ($H_2WO_4$), as form, for example on dissolution of tungsten trioxide in aqueous ammonia, ie. monotungstates, and also the isopolytungstates forming therefrom on acidification, for example the paratungstates or metatungstates, ammonium heptamolybdate or $CrCl_3$, may be used as oxide precursors of this type.

The application may be effected in one step or in a plurality of steps if the solubility of the oxide precursor is too low. If impregnation is carried out several times, the catalyst is also dried and calcined in between. If a plurality of oxides are to be applied to the carrier, this may be effected in one or more steps. What is decisive here is whether it is possible to find conditions which are compatible with the simultaneous application of both oxides in the desired amounts. If this is not the case, the two oxides are applied in succession and drying and calcination may be carried out in between. The order of the application may influence the catalysis and should therefore be optimized for the individual combination of oxides.

If the chosen carrier has a high ion exchange capacity, as is the case, for example, with sheet silicates or amorphous aluminosilicates, the application of the oxide precursors may also be effected by means of ion exchange. For this purpose, the carrier is brought into contact continuously or batchwise with an excess of solution of the oxide precursors so that the exchangeable ions of the carrier are exchanged for those of groups IVB and/or VIB.

The calcination of the catalyst precursors after application of the oxide precursors to the carriers leads to the conversion of the oxide precursors into the catalytically active oxides. Depending on the duration of the calcination and on the chosen oxide or oxide precursor, the temperature is from 250° to 800° C., preferably from 300° to 600° C.

The catalysts are generally prepared by steeping or impregnating moldings of the carrier. However, it is also possible to load the carrier in powder form with the oxides or precursors thereof and then to mold the material by one of the conventional methods. Binders may be used for this molding procedure, but inorganic binders reduce the content of active material in the prepared moldings.

The novel oxides of groups IVB or VIB or mixtures thereof on carriers may be modified in various ways to increase the selectivity, the time-on-stream and the number of possible regenerations.

One modification of the catalysts comprises subjecting the unmolded or the molded oxides of group IVB or VIB or mixtures thereof on carriers to ion exchange or doping with (other) transition metals, such as Sc, Mn, Fe, Nb, Cu or Zn, or noble metals and/or rare earth metals, such as La, Ce or Y.

In one advantageous embodiment, the molded novel oxides of group IVB or VIB or mixtures thereof on carriers are initially taken in a flow tube and, for example, a halide, an acetate, an oxalate, a citrate or a nitrate of the metals described above, in dissolved form, is passed over at from 20° to 100° C. Ion exchange of this type can be carried out, for example, on the hydrogen, ammonium and alkali metal form of the novel oxides of group IVB or VIB or mixtures thereof on carriers.

A further possibility of applying metal to the novel oxides of group IVB or VIB or mixtures thereof on carriers is to impregnate the material, for example with a halide, a nitrate, an acetate, an oxalate, a citrate or an oxide of the metals described above, in aqueous or alcoholic solution.

Both ion exchange and impregnation may be followed by drying and, if desired, repeated calcination. In the case of metal-doped oxides of group IVB or VIB or mixtures thereof on carriers, an aftertreatment with hydrogen and/or with steam may be advantageous.

A further possibility for modification comprises subjecting the novel oxides of group IVB or VIB or mixtures thereof on carriers—in the molded or unmolded state—to a treatment with acids, such as hydrochloric acid (HCl), hydrofluoric acid (HF), sulfuric acid ($H_2SO_4$), oxalic acid ($HO_2C—CO_2H$) or phosphoric acid ($H_3PO_4$).

In a particular embodiment, the novel oxides of group IVB or VIB or mixtures thereof on carriers are refluxed, prior to the molding procedure, with one of the stated 0.001–2N, preferably 0.05–0.5N, acids for from 1 to 100 hours. Separation by filtration and thorough washing are followed, as a rule, by drying at from 100° to 160° C. and calcination at from 200° to 600° C. A further particular embodiment comprises acid treatment of the novel oxides of group IVB or VIB or mixtures thereof on carriers after they have been molded with binders. Here, the novel oxides of group IVB or VIB or mixtures thereof on carriers are treated, as a rule, for from 1 to 3 hours at from 60° to 80° C., with a 3–25, in particular 12–20, % strength acid and are then thoroughly washed, dried at from 100° to 160° C. and calcined at from 200° to 600° C.

Another possibility for modification involves exchange with ammonium salts, for example with $NH_4Cl$, or with mono-, di- or polyamines. Here, the molded oxide of group IVB or VIB or mixture of said oxides on a carrier is subjected to exchange, as a rule, at from 60° to 80° C., with from 10 to 25, preferably 20, % strength $NH_4Cl$ solution continuously for 2 hours in a solution having a weight ratio of oxide to ammonium chloride of 1:15, and is then dried at from 100° to 120° C.

The catalysts may be used for the amination of the olefins in the form of extrudates having diameters of, for example, from 1 to 4 mm, in the form of beads or in the form of pellets having a diameter of, for example, from 3 to 5 mm.

Fluidized material having a size of 0.1 to 0.8 mm may be obtained from the catalyst, molded for example to give extrudates, by milling and sieving.

$R^1$, $R^2$, $R^3$, $R^4$, $R^5$ and $R^6$ in the compounds I, II and III have the following meanings:

$R^1$, $R^2$, $R^3$, $R^4$, $R^5$ and $R^6$ are each
hydrogen,
$C_1$–$C_{20}$-alkyl, preferably $C_1$–$C_{12}$-alkyl, particularly preferably $C_1$–$C_8$-alkyl, such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl or isooctyl,
$C_2$–$C_{20}$-alkenyl, preferably $C_2$–$C_{12}$-alkenyl, particularly preferably $C_2$–$C_8$-alkenyl, such as vinyl or allyl,
$C_2$–$C_{20}$-alkynyl, preferably $C_2$–$C_8$-alkynyl, in particular $C_2H$ or propargyl,
$C_3$–$C_{20}$-cycloalkyl, preferably $C_3$–$C_{12}$-cycloalkyl, particularly preferably $C_5$–$C_8$-cycloalkyl, such as cyclopentyl, cyclohexyl, cycloheptyl or cyclooctyl,
$C_4$–$C_{20}$-alkylcycloalkyl, preferably $C_4$–$C_{12}$-alkylcycloalkyl, particularly preferably $C_5$–$C_{10}$-alkylcycloalkyl,
$C_4$–$C_{20}$-cycloalkylalkyl, preferably $C_4$–$C_{12}$-cycloalkylalkyl, particularly preferably $C_5$–$C_{10}$-cycloalkylalkyl,
aryl such as phenyl, 1-naphthyl or 2-naphthyl, preferably phenyl,
$C_7$–$C_{20}$-alkylaryl, preferably $C_7$–$C_{16}$-alkylaryl, particularly preferably $C_7$–$C_{12}$-alkylphenyl such as 2-methylphenyl, 3-methylphenyl, 4-methylphenyl, 2-ethylphenyl, 3-ethylphenyl or 4-ethylphenyl,
$C_7$–$C_{20}$-aralkyl, preferably $C_7$–$C_{16}$-aralkyl, particularly preferably $C_7$–$C_{12}$-phenalkyl such as phenylmethyl, 1-phenylethyl or 2-phenylethyl,
$R^1$ and $R^2$
together form a saturated or unsaturated $C_3$–$C_9$-alkylene chain, preferably —$(CH_2)_4$—, —$(CH_2)_5$—, —$(CH_2)_7$— or —CH=CH—CH=CH—,
$R^3$ or $R^5$ is
$C_{21}$–$C_{200}$-alkyl, preferably $C_{40}$–$C_{200}$-alkyl, such as polybutyl, polyisobutyl, polypropyl, polyisopropyl or polyethyl, particularly preferably polybutyl or polyisobutyl,
$C_{21}$–$C_{200}$-alkenyl, preferably $C_{40}$–$C_{200}$-alkenyl, particularly preferably $C_{70}$–$C_{170}$-alkenyl, $R^3$ and $R^5$
together form a $C_2$–$C_{12}$-alkylene chain, preferably a $C_3$–$C_8$-alkylene chain, particularly preferably —(CH$_2$)$_3$—, —(CH$_2$)$_4$—, —(CH$_2$)$_5$—, —(CH$_2$)$_6$— or —(CH$_2$)$_7$—, particular —(CH$_2$)$_3$— or —(CH$_2$)$_4$—.

EXAMPLES

Catalyst syntheses
Catalyst A (Comparative Example): SiO$_2$ (D11-190®)

Catalyst A consisted of pure SiO$_2$ extrudate (4 mm) from BASF (D11-10®). The BET surface area was 173 m$^2$g$^{-1}$.
Catalyst B (Comparative Example): SiO$_2$ (Siliperl®)

Catalyst B consisted of pure SiO$_2$ beads (from 1.5 to 3.5 mm) from Engelhardt (Siliperl® AF125). The BET surface area was 300 m$^2$g$^{-1}$.
Catalyst C: WO$_3$—ZrO$_2$/SiO$_2$ 534 g of zirconium carbonate were dissolved in 813 g of 65% strength HNO$_3$ and the solution was sprayed on to 820 g of catalyst B in the course of 40 minutes by means of a nozzle. The catalyst impregnated in this manner was dried and was calcined at 450° C. for 2 hours. 116 g of H$_2$WO$_4$, dissolved in 666 g of aqueous NH$_3$ (25% strength), were then applied in the course of 20 minutes. The catalyst impregnated in this manner was dried and was calcined at 350° C. for 2 hours. Catalyst C contained 15.5% by weight of zirconium and 8.4% by weight of tungsten.
Catalyst D: WO$_3$—ZrO$_2$/SiO$_2$ 40 g of catalyst C were calcined at 600° C. for 2 hours. Catalyst D contained 12.1% by weight of zirconium and 7.8% by weight of tungsten and had a BET surface area of 228 m$^2$g$^{-1}$.
Catalyst E: WO$_3$—ZrO$_2$/SiO$_2$ 577 g of zirconium carbonate were dissolved in 800 g of 65% strength HNO$_3$ and the solution was sprayed on to 600 g of catalyst A in the course of 25 minutes by means of a nozzle. The catalyst impregnated in this manner was dried and was calcined at 450° C. for 2 hours. 120 g of H$_2$WO$_4$ were then dissolved in 690 g of aqueous NH$_3$ (25% strength) and applied in the course of 30 minutes. The catalyst impregnated in this manner was dried and was calcined at 350° C. for 2 hours. Catalyst E contained 15.5% by weight of zirconium and 8.4% by weight of tungsten.
Catalyst F: ZrO$_2$/SiO$_2$ 100 g of catalyst A were dried, and a solution of 2.7 g of ZrO(NO$_3$)$_2$.H$_2$O in 100 g of distilled water were added. The water was slowly stripped off under reduced pressure and calcination was then carried out at 350° C. for 5 hours. Catalyst F contained 1% by weight of zirconium and had a BET surface area of 190 m$^2$g$^{-1}$.
Catalyst G: WO$_3$/SiO$_2$ 100 g of catalyst A were dried, and a solution of 12.5 g of H$_2$WO$_4$ in 100 g of aqueous NH$_3$ (25% strength) was added. The water was slowly stripped off under reduced pressure and calcination was then carried out at 350° C. for 5 hours. Catalyst G contained 7.6% by weight of tungsten and had a BET surface area of 132 m$^2$g$^{-1}$.
Catalyst H (Comparative Example): Fe$_2$O$_3$/SiO$_2$ 100 g of catalyst A were dried, and a solution of 38 g of Fe(NO$_3$)$_3$.9H$_2$O in 95 g of distilled water was added. The water was slowly stripped off under reduced pressure and calcination was then carried out at 500° C. for 2 hours. Catalyst H contained 4.7% by weight of iron and had a BET surface area of 181 m$^2$g$^{-1}$.
Catalyst I: ZrO$_2$/SiO$_2$ 100 g of catalyst A were dried, and a solution of 5.6 g of ZrO(NO$_3$)$_2$.H$_2$O in 100 g of distilled water was added. The water was slowly stripped off under reduced pressure and calcination was then carried out at 500° C. for 2 hours. Catalyst I contained 1.9% by weight of zirconium and had a BET surface area of 180 m$^2$g$^{-1}$.
Catalyst J: WO$_3$—ZrO$_2$/SiO$_2$ 100 g of catalyst A were dried, and a solution of 2.7 g of ZrO(NO$_3$)$_2$.H$_2$O in 100 g of distilled water was added. The water was slowly stripped off under reduced pressure and drying was then carried out at 120° C. for 3 hours. A solution of 1.4 g of H$_2$WO$_4$ in 100 g of aqueous NH$_3$ (32% strength) was then added. The water was slowly stripped off under reduced pressure and calcination was carried out at 500° C. for 2 hours. Catalyst J contained 0.9% by weight of zirconium and 1% by weight of tungsten and had a BET surface area of 138 m$^2$g$^{-1}$.
Catalyst K: WO$_3$/SiO$_2$ 100 g of catalyst A were dried, and a solution of 25 g of H$_2$WO$_4$ in 100 g of aqueous NH$_3$ (32% strength) was added. The water was slowly stripped off under reduced pressure and calcination was then carried out at 500° C. for 2 hours. Catalyst K contained 14.5% by weight of tungsten and had a BET surface area of 107 m$^2$g$^{-1}$.
Catalyst L: ZrO$_2$/SiO$_2$ 75 g of catalyst A were dried, and a solution of 20.5 g of ZrO(NO$_3$)$_2$.H$_2$O in 75 g of distilled water was added. The water was slowly stripped off under reduced pressure and calcination was then carried out at 350° C. for 5 hours. Catalyst L contained 8.6% by weight of zirconium.

Amination examples

The experiments were carried out in a tube reactor (6 mm internal diameter) under isothermal conditions and from 260° to 300° C. and 280 bar with a mixture of isobutene and ammonia in a molar ratio of 1:1.5. The reaction products were analyzed in a gas chromatograph.

The results are listed in Table 1 and show that the novel catalysts have substantially higher yields than the pure carriers. Other oxides exhibit low activity.

TABLE 1

| | | | tert-Butylamine (NH$_3$:C$_4$H$_8$ = 1.5) | | | |
|---|---|---|---|---|---|---|
| | | Tem- | tert-Butylamine yield | | | Weight |
| Cata-lyst No. | Pres-sure [bar] | per-ature [°C.] | WHSV 0.7 [g/g · h] | [% by weight] WHSV 1.5 [g/g · h] | WHSV 3 [g/g · h] | by liter [kg/l] |
| A | 280 | 300 | 2.01 | 0.92 | 0.52 | 0.37 |
| B | 280 | 300 | 3.35 | 1.76 | 0.88 | 0.41 |
| C | 280 | 300 | 13.47 | 10.42 | 7.30 | 0.54 |
| D | 280 | 300 | 9.84 | 7.93 | 4.45 | 0.58 |
| E | 280 | 300 | 14.07 | 11.78 | 7.26 | 0.53 |
| F | 280 | 300 | 7.50 | 3.83 | 2.01 | 0.38 |
| G | 280 | 300 | 11.64 | 7.15 | 4.03 | 0.38 |
| H | 280 | 300 | 1.19 | 0.26 | | 0.39 |
| I | 280 | 300 | 5.00 | 2.54 | 1.35 | 0.38 |
| J | 280 | 300 | 6.02 | 3.42 | | 0.38 |
| K | 280 | 300 | 8.97 | 5.38 | 3.68 | 0.40 |
| L | 280 | 300 | 5.34 | 3.42 | 2.28 | 0.40 |

We claim:

1. A process for the preparation of amines of the formula

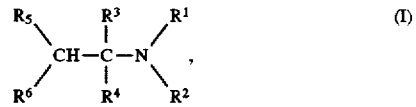

where
$R^1$, $R^2$, $R^3$, $R^4$, $R^5$ and $R^6$ are each hydrogen, $C_1$–$C_{20}$-alkyl, $C_2$–$C_{20}$-alkenyl, $C_2$–$C_{20}$-alkynyl, $C_3$–$C_{20}$- cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl, $R^1$ and $R^2$ together form a saturated or unsaturated $C_3$–$C_9$-alkylene chain and $R^3$ or $R^5$ is $C_{21}$–$C_{200}$-alkyl or $C_{21}$–$C_{200}$-alkenyl, or $R^3$ and $R^5$ together form a $C_2$–$C_{12}$-alkylene chain, by reacting an olefin of the formula II

   (II)

where $R^3$, $R^4$, $R^5$ and $R^6$ have the abovementioned meanings, with ammonia or a primary or secondary amine of the formula III

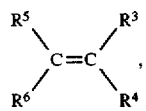   (III)

where $R^1$ and $R^2$ have the abovementioned meanings, at from 200° to 350° C. and from 100 to 300 bar in the presence of a heterogeneous catalyst, wherein the heterogeneous catalyst used is an oxide of group IVB or VIB or a mixture thereof on a carrier.

2. A process as claimed in claim 1 for the preparation of amines I, wherein the amine I formed is separated off and the unconverted starting materials II and III are recycled.

3. A process as claimed in claim 1 for the preparation of amines, wherein the olefin II used is isobutene, diisobutene, cyclopentene, cyclohexene or polyisobutene.

4. A process as claimed in claim 1 for the preparation of amines, $TiO_2$, $ZrO_2$, $HfO_2$, $Cr_2O_3$, $CrO_2$, $CrO_3$, $MoO_2$, $MoO_3$, $WO_2$, $WO_3$ or a mixture thereof is used as oxides of groups IVB and VIB.

5. A process as claimed in claim 1 for the preparation of amines, wherein $WO_3$, $ZrO_2$ or a mixture thereof on a carrier is used.

6. A process as claimed in claim 1 for the preparation of amines, wherein a heterogeneous catalyst which contains from 5 to 15% by weight of tungsten and from 8 to 25% by weight of zirconium on a carrier is used.

7. A process as claimed in claim 1 for the preparation of amines, wherein oxides of groups IVB or VIB or mixtures thereof on carriers are used as heterogeneous catalysts which are essentially free of alkali metal ions or alkaline earth metal ions.

8. A process as claimed in claim 1 for the preparation of amines, wherein oxides of groups IVB or VIB or mixtures thereof on carriers are used as heterogeneous catalysts which are additionally doped with one or more transition metals or with one or more rare earth elements.

9. A process as claimed in claim 1 for the preparation of amines, wherein the carrier comprises from 60 to 100% by weight of silica.

10. A process as claimed in claim 1 for the preparation of amines, wherein a heterogeneous catalyst having a BET surface area of from 100 to 1000 $m^2g^{-1}$ is used.

11. A process as claimed in claim 1 for the preparation of amines, wherein a heterogeneous catalyst having a BET surface area of from 120 to 600 $m^2g^{-1}$ is used.

* * * * *